United States Patent [19]
Poli

[11] Patent Number: 4,854,155
[45] Date of Patent: Aug. 8, 1989

[54] COMBUSTIBLE GAS DETECTOR HAVING CATALYTIC SENSOR STABILIZING NETWORK

[75] Inventor: Albert A. Poli, Pittsburgh, Pa.
[73] Assignee: Mine Safety Appliances Company, Pittsburgh, Pa.
[21] Appl. No.: 259,760
[22] Filed: Oct. 19, 1988
[51] Int. Cl.[4] .............................................. G01N 27/18
[52] U.S. Cl. .................................................. 73/27 R
[58] Field of Search ............... 73/27 R, 118.2; 422/96

[56] References Cited

U.S. PATENT DOCUMENTS

| | | | |
|---|---|---|---|
| 3,519,391 | 7/1970 | Winter et al. | 73/27 R X |
| 4,011,538 | 3/1977 | Froemel | 73/27 R X |
| 4,123,934 | 11/1978 | Höht | 73/27 R |
| 4,196,622 | 4/1980 | Peter | 73/118.2 |
| 4,341,114 | 7/1982 | Plapp | 73/118.2 |
| 4,373,383 | 2/1983 | Plapp et al. | 73/118.2 |
| 4,420,971 | 12/1983 | Rapps et al. | 73/118.2 |
| 4,451,816 | 5/1984 | Ball | 73/27 R X |

FOREIGN PATENT DOCUMENTS 1405603  9/1975  United Kingdom ............... 73/27 R

*Primary Examiner*—Tom Noland
*Assistant Examiner*—Joseph W. Roskos
*Attorney, Agent, or Firm*—Douglas K. McClaine

[57] ABSTRACT

A catalytic gas detector circuit in which the temperature of a resistance gas sensing element, contained in a bridge circuit, is temporarily increased by energizing a current changing network for a finite period of time sufficiently long enough to burn impurities off of the surface of the sensing element.

6 Claims, 1 Drawing Sheet

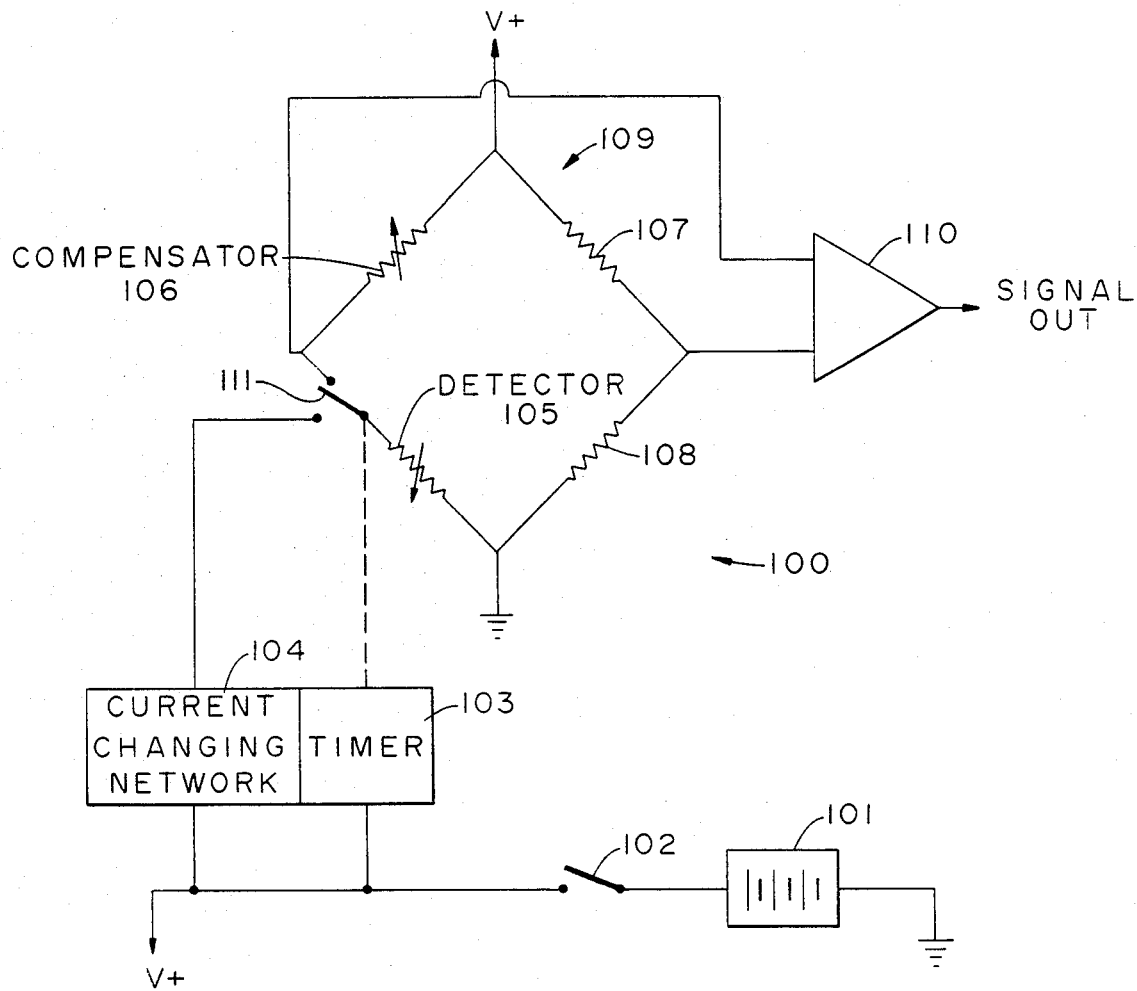

COMBUSTIBLE GAS DETECTOR HAVING CATALYTIC SENSOR STABILIZING NETWORK

FIELD OF THE INVENTION

This invention is related to the field of combustible gas detectors having catalytic-coated resistance sensing elements.

BACKGROUND OF THE INVENTION

Traditionally, combustible gas detectors used to detect the presence of combustible gases, such as those found in coal mines or manufacturing facilities, utilized a circuit configuration comprised of at least one sensing element. This sensing element was a wire having a catalytic coating sensitive to a gas. The sensing element was used as one of four legs of a Wheatstone bridge circuit. The other three legs consisted of two resistors and a compensator element. The compensator element was identical to the sensing element except that it did not bear a catalytic coating.

A current or voltage was applied to the bridge circuit to heat the surface of the catalytic coating affixed to the sensing element. Since the resistance values of the other three legs of the bridge were known, the resistance in the sensing element could be determined as the current or voltage was passed through the bridge.

When the sensing element was exposed to a combustible gas, such as methane, the catalytic coating would begin to burn the gas, increasing the temperature of the sensing element. As the temperature of the sensing element increased, the resistance of the element increased. Accordingly, the current or voltage passing through the element decreased. By comparing the resistance level of the sensing element to the resistance level of the compensator element, the presence of a combustible gas could be detected. Since a change in the gas concentration caused a change in the resistance of the sensing element, the quantity of the gas could be accurately determined by calibrating the change in resistance. This is the basic principle of operation of a catalytic combustible gas sensor.

Catalytic sensing elements can be, for example, a wire having a palladium bead coating (hereinafter referred to as a "pelement") or a wire filament that is coated with platinum. Sensing elements of the
type mentioned are disclosed in Baker, U.S. Pat. No. 3,092,799. The catalytic coating of a pelement provides a large number of active sites that promote combustion of the flammable gas.

Over a period of time, the sensitivity of the pelement tends to diminish. This reduced sensitivity most often occurs in instruments that are used intermittently. Intermittent use of the instrument causes the pelement to be heated when the instrument is turned on and then cooled when the instrument is shut off. When a high temperature in the pelement is not maintained, certain components found in the test gas do not burn completely. These components, known as inhibitors, tend to occlude, foul or poison the active sites found on the pelement surface. As these sites become poisoned, less test gas is burned on the pelement's surface, causing a reduction of surface temperature and decreased sensitivity.

The inhibitors can be burnt off the active sites by driving a high current through the pelement for a short period of time. It is the intent of this invention to provide a combustible gas detector having a circuit to enable a high current to be driven through the catalytic sensing element for a specific period of time in order to maintain the instrument's accuracy and reliability.

SUMMARY OF THE INVENTION

In accordance with the present invention, a new and improved catalytic combustible gas detector configuration is provided that overcomes the disadvantages of other prior art circuits used in portable gas detecting instruments. Specifically, the invention provides a bridge circuit where one of the four branches of the bridge is a sensing element and one of the other branches is a compensator element. A current or voltage is applied to the circuit and the individual resistances of the compensator element and the sensing element are determined. The elements are then exposed to a combustible gas and the new resistance of the sensing element is compared to the resistance of the compensating element. The difference in resistance between the sensing element and the compensator element is then calibrated to show the concentration of a test gas in the test sample.

In order to eliminate inhibitors or poisons that build up on the pelement, an electronically-timed switch is added to the instrument unit to provide a high current flow through the pelement for a period of time. The timer provides a current that is approximately one-third higher than the current that is initiated each time the instrument is turned on. The high current passes through the pelement, causing the pelement surface temperature to increase. This increased temperature causes the inhibitors to be burnt off of the active sites of the pelement. After the specified time, the current is reduced to the proper operating current for the instrument.

These features and other objectives of the invention will become apparent from the following detailed description taken in connection with the accompanying drawing.

BRIEF DESCRIPTION OF THE DRAWINGS

The drawing is a schematic circuit diagram of the gas detector having a catalytic sensor stabilizing network.

DESCRIPTION OF THE PREFERRED EMBODIMENT

With reference to the drawing, a circuit diagram 100 of a combustible gas sensor is shown. A power supply 101 provides either constant voltage or constant current (hereinafter "current") of approximately 0.4 amps to an on/off switch 102. When the on/off switch 102 is closed, the current activates a solid state timer 103. The timer 103 closes a switch 111 that is positioned in the sensor (detector) arm 105 of a Wheatstone bridge circuit 109. The timer 103 also controls a current changing network 104 that boosts the current to approximately 0.6 amps. This increased current is applied to the sensor (detector) arm 105 of the Wheatstone bridge circuit 109 through the switch 111. The other three legs of the bridge circuit are comprised of a compensator element 106 and two resistors 107 and 108 of approximately 1000 ohms each. The bridge circuit is capable of operating in either a constant voltage mode, a constant current mode, a constant temperature mode or a constant resistance mode. The compensator element 106 is identical to the sensing element 105 except that it does not bear a catalytic coating. The resistance change in the bridge circuit 109 causes a current change that causes a difference signal to be sent out to a readout device by means of a differential amplifier 110. The signal is calibrated to indicate the quantity of the tested gas by comparing the resistances of the compensator element 106 and detector element 105.

While the timer 103 continues to operate the current changing network 104, the detector element 105 is exposed to a current approximately one-third higher than the normal operating current seen in the bridge. The increased current heats the detector element 105 to burn inhibitors from the detector element 105. The timer 103 continues to operate for a predetermined time to sufficiently burn off the impurities and then opens the switch 111 in the detector branch 105 of the Wheatstone bridge circuit 109 while shutting off the current amplifier 104. This reduces the current seen by the detector element to a normal operating level. The impurities on the detector element 105 have effectively been removed by the higher current and, accordingly, the sensitivity level of the detector element 105 has been restored.

The timer 103 is set to operate each time that the instrument is turned on. Once the timer 103 turns off, the circuit is ready to sense the presence of a combustible gas, such as a hydrocarbon gas. When the sensing element 105 is exposed to the combustible gas, the catalytic coating of the sensing element 105 promotes combustion. As the temperature of the sensing element 105 increases, the resistances between the sensing element 105 and the compensator element 106 become unbalanced. This resistance imbalance is measured by a differential amplifier 110 that generates a signal to a calibrated readout gauge (not shown). The gauge is calibrated to indicate the concentration of the test gas as a function of the degree of resistance imbalance.

The invention has been described in its preferred embodiment. It is readily apparent that there are numerous modifications and variations of the present invention that may be made possible by the above teachings while still remaining within the scope of the appended claims.

What is claimed is:

1. A catalytic gas detector circuit comprising:
   a bridge circuit having four branches and having input and output terminals wherein said input terminals are connected to a power source means and said output terminals are connected to a means to measure an imbalance in said bridge;
   said first branch is a catalytic gas sensing element that is reactive to combustible gases;
   said second branch is a compensating element;
   said third and fourth branches are resistors;
   a current changing means to temporarily increase a normal operating current of said circuit for a predetermined period of time sufficient to exceed the normal operating temperature of said catalytic gas sensing element off and remove inhibitors from said catalytic gas sensing element wherein said current changing means is connected between said bridge and said power source; and,
   a timer means to activate said current changing means for said predetermined period of time.

2. The detector circuit according to claim 1 wherein said current changing means is a current amplifier.

3. The detector circuit according to claim 1 wherein said timer means is a solid state integrated circuit.

4. The detector circuit according to claim 1 where said catalytic gas sensing element comprises a catalytic coating.

5. The detector circuit according to claim 1 where said catalytic gas sensing element comprises a coiled platinum filament imbedded in a catalytic bead.

6. The detector circuit according to claim 1 where said current changing means produces currents in a range of one-third higher than normal operating current.

* * * * *